United States Patent [19]

Broadhurst et al.

[11] Patent Number: 4,994,488
[45] Date of Patent: Feb. 19, 1991

[54] IMIDATE INSECTICIDES

[75] Inventors: Michael D. Broadhurst, Novato; Karl J. Fisher, Fairfax; William G. Haag, Martinez; Michael R. Leadbetter, El Cerrito, all of Calif.

[73] Assignee: ICI Americas Inc., Wilmington, Del.

[21] Appl. No.: 343,550

[22] Filed: Apr. 27, 1989

Related U.S. Application Data

[63] Continuation-in-part of Ser. No. 263,605, Oct. 31, 1988, which is a continuation-in-part of Ser. No. 264,746, Oct. 31, 1988, which is a continuation-in-part of Ser. No. 122,877, Nov. 17, 1987, abandoned.

[51] Int. Cl.$^5$ .............................. A61K 31/21
[52] U.S. Cl. .................... 514/508; 514/357; 514/351; 514/466; 558/9; 549/562; 546/300
[58] Field of Search ................ 558/9; 549/562; 514/508

[56] References Cited

U.S. PATENT DOCUMENTS

| | | | |
|---|---|---|---|
| 3,832,351 | 8/1974 | Tanaka et al. | 260/298.4 |
| 3,847,988 | 11/1974 | Gold | 71/107 |
| 3,899,582 | 8/1975 | Tanaka et al. | 71/107 |
| 4,254,264 | 3/1981 | Kohn et al. | 546/291 |
| 4,256,893 | 3/1981 | Malhotra | 540/301 |
| 4,261,920 | 4/1981 | Fuchs et al. | 260/405 |
| 4,272,449 | 6/1981 | Kohn et al. | 260/453.99 |
| 4,285,879 | 8/1981 | Kohn et al. | 260/453.7 |
| 4,288,621 | 9/1981 | Kohn et al. | 564/190 |
| 4,329,518 | 5/1982 | Plummer | 568/807 |
| 4,370,346 | 1/1983 | Punja | 424/305 |
| 4,594,355 | 6/1986 | Elliott et al. | 514/521 |
| 4,692,187 | 9/1987 | Kiehs et al. | 71/107 |

FOREIGN PATENT DOCUMENTS

| | | | |
|---|---|---|---|
| 6155 | 1/1980 | European Pat. Off. | 71/107 |
| 196156 | 10/1986 | European Pat. Off. | 71/107 |
| 211561 | 2/1987 | European Pat. Off. | 71/107 |
| 239535 | 9/1987 | European Pat. Off. | 546/301 |
| 271240 | 6/1988 | European Pat. Off. | 71/107 |
| 2944849 | 6/1981 | Fed. Rep. of Germany | 71/107 |
| 23775 | 2/1989 | Iran | 71/107 |
| 49-27331 | 7/1974 | Japan | 71/106 |
| 50-94133 | 7/1975 | Japan | 71/107 |
| 549342 | 5/1974 | Switzerland | 71/106 |
| 2122616 | 1/1984 | United Kingdom | 71/107 |

OTHER PUBLICATIONS

Elliott et al., J. Chem. Soc. (C) (1971), pp. 2551–2554.
Elliott et al., J. Sci. Food & Agricultural, vol. 18, pp. 167–171 (1967).
Plummer et al., Pesticide Science, vol. 14, pp. 560–570 (1983).
Tanaka et al., Agricultural & Biological Chemistry, vol. 41, pp. 1953–1959 (1977).
Naumann, Chemie der Pflanzenschutzund Schadlings-bekampfungsmittel, vol. 7, pp. 70–74, 76–77, 82–83 (1981).

*Primary Examiner*—James H. Reamer
*Attorney, Agent, or Firm*—Joel G. Ackerman

[57] ABSTRACT

A series of novel imidate insecticides distinguished by the general formula

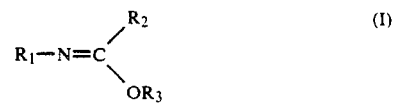

in which $R_1$ is an optionally substituted aryl group in which the substituents are halo, $C_1$–$C_4$ alkyl, $C_1$–$C_4$ haloalkoxy, $C_1$–$C_4$ alkoxy, $C_1$–$C_4$ haloalkylthio, $C_3$–$C_6$ cycloalkyl, nitro, $C_1$–$C_4$ haloalkyl, $C_2$–$C_5$ carboalkoxy, $C_1$–$C_4$ alkylthio, cyano, $C_1$–$C_4$ alkylsulfonyl, $C_1$–$C_4$ haloalkylsulfonyl, $C_2$–$C_5$ alkylcarbonyl, $C_2$–$C_4$ alkyleneoxy, $C_1$–$C_2$ perhaloalkyleneoxy, $C_1$–$C_4$ alkylenedioxy, $C_1$–$C_3$ halo-substituted alkylenedioxy, phenyl, mono-substituted phenyl, pyridyloxy, $C_2$–$C_4$ alkylene, $C_2$–$C_4$ alkenyl, $C_3$-haloalkenoxy, and/or amido;

$R_2$ is cyclopropyl or mono- or poly- halo- or methyl-substituted cyclopropyl; and $R_3$ is (a) an optionally substituted 3-phenoxyphenalkyl, 3-phenoxypyridylalkyl, 3-(pyridyloxy)phenalkyl moiety; 3-phenylaminophenalkyl, 3-benzylphenalkyl or benzyloxyphenalkyl moiety; (b) a benzylfuranylmethyl moiety; (c) a 3- or 4-substituted benzyl or tetrafluorobenzyl moiety; (d) 4-phenoxy-2-butyn-2-yl; (e) 2-methyl-3-phneylbenzyl, or (f) 4-(4-trifluoromethyl-2-pyridyloxy)benzyl.

26 Claims, No Drawings

IMIDATE INSECTICIDES

CROSS REFERENCE TO RELATED APPLICATIONS

This is a continuation-in-part of application Ser. No. 263,605, filed Oct. 31, 1988 and of application Ser. No. 264,746, filed Oct. 31, 1988, both of which are continuations-in-part of application Ser. No. 122,877, filed Nov. 17, 1987 now abandoned.

This invention relates to a series of novel imidate insecticides distinguished by the general formula

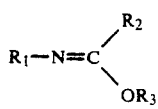

in which $R_1$ is an optionally substituted aryl group in which the substituents are halo, $C_1-C_4$ alkyl, $C_1-C_4$ haloalkoxy, $C_1-C_4$ alkoxy, $C_1-C_4$ haloalkylthio, $C_3-C_6$ cycloalkyl, nitro, $C_1-C_4$ haloalkyl, $C_2-C_5$ carboalkoxy, $C_1-C_4$ alkylthio, cyano, $C_1-C_4$ alkysulfonyl, $C_1-C_4$ haloalkylsulfonyl, $C_2-C_5$ alkylcarbonyl, $C_2-C_4$ alkyleneoxy, $C_1-C_2$ perhaloalkyleneoxy, $C_1-C_4$ alkylenedioxy, $C_1-C_3$ halo-substituted alkylenedioxy, phenyl, mono-substituted phenyl, pyridyloxy, $C_2-C_4$ alkylene, $C_2-C_4$ alkenyl, $C_3$-haloalkenoxy, and/or amido;

$R_2$ is cyclopropyl or mono- or poly- or halo- or methyl-substituted cyclopropyl; and $R_3$ is (a) an optionally substituted 3-phenoxyphenalkyl, 3-phenoxypyridylalkyl, 3-(pyridyloxy)phenalkyl, 3-phenylaminophenalkyl, 3-benzylphenalkyl or benzyloxyphenalkyl moiety; (b) a benzylfuranylmethyl moiety; (c) a 3- or 4-substituted benzyl or tetrafluorobenzyl moiety; (d) 4-phenoxy-2-butyn-2-yl; (e) 2-methyl-3-phenylbenzyl; or (f) 4-(4-trifluoromethyl-2-pryidyloxy) benzyl.

Compounds of this invention demonstrate activity in controlling various types of insects, including lepidoptera, hemiptera and coleoptera, particularly in foliar application.

Another aspect of this invention involves insecticidal compositions comprising an insecticidally effective amount of a compound of the invention with an insecticidally suitable diluent or carrier.

In another aspect, this invention involves a method for controlling insects by administration of an insecticidally effective amount of a compound or composition of this invention to a locus where control is desired.

The term "insects" as used herein refers to the broad and commonly understood usage rather than to those creatures which in the strict biological sense are classified as insects. In addition to those belonging to the class Insecta, this term includes some classes of acarids such as mites and the like.

More particularly, the compounds of formula (I) are those in which:

$R_1$ is a naphthyl, optionally substituted by up to 2 halogens; or phenyl, optionally substituted by one or more of the following: $C_2-C_5$ carboalkoxy, $C_1-C_4$ alkylsulfonyl, $C_1-C_4$ haloalkylsulfonyl, $C_2-C_5$ alkylcarbonyl, $C_2-C_4$ alkenyl, $C_3$-haloalkenoxy, $C_1-C_4$ haloalkylthio, $C_3-C_6$ cycloalkyl, phenyl, monosubstituted phenyl, pyridyloxy, $C_2-C_4$ alkyleneoxy, $C_1-C_2$ perhaloalkyleneoxy, $C_1-C_4$ alkylenedioxy, $C_1-C_3$ halo-alkylenedioxy, $C_2-C_4$ alkylene, amido, nitro, cyano, up to two $C_1-C_4$ alkylthio groups, up to three $C_1-C_4$ alkoxy groups, up to three $C_1-C_4$ haloalkoxy groups, up to three $C_1-C_4$ alkyl groups, up to three $C_1-C_4$ haloalkyl groups, or up to five halogens; $R_2$ is cyclopropyl, optionally substituted by up to 4 methyl groups or up to 2 halogens; and $R_3$ is:

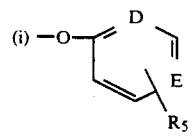
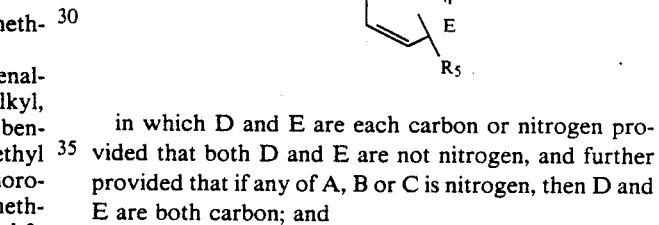

in which m is 0 or 1;

A, B and C are each carbon or nitrogen, provided that A, B and C are not all nitrogen and if two of A, B and C are nitrogen, then A and C are nitrogen;

$R_4$ is hydrogen, monohalo or dihalo;

$R_6$ is hydrogen, methyl, fluoro or ethynyl; and $R_7$ is (i)

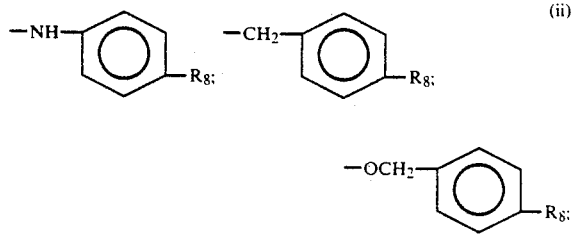

in which D and E are each carbon or nitrogen provided that both D and E are not nitrogen, and further provided that if any of A, B or C is nitrogen, then D and E are both carbon; and $R_5$ is hydrogen, $C_1-C_4$ alkyl, $C_1-C_4$ alkoxy, trifluoromethyl, cyano, $C_1-C_4$ alkylthio, $C_1-C_4$ alkylsulfonyl, or mono- or polyhalo;

(ii)

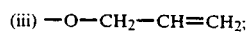

in which $R_8$ is hydrogen or halogen; or (iii) $-O-CH_2-CH=CH_2$;

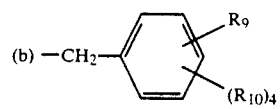

in which (i) $R_9$ is 4-fluoro, 4-methoxymethyl, or 4-propargyl, and $R_{10}$ is fluoro or (ii) $R_9$ is 3- or 4-allyl, 3- or 4-propargyl, or 3- or 4-(mono- or dihalo)allyl, and $R_{10}$ is hydrogen or fluoro;

(c) 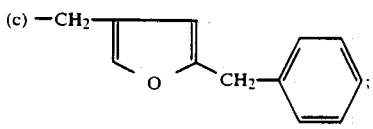

(d) 4-phenoxy-2-butyn-2yl;
(e) 3-bromo-4-fluorobenzyl;
(f) 4-(benzyloxy)benzyl;
(g) 4-(4-fluorobenzyloxy)benzyl;

4-(4-fluorobenzylozy)benzyl;  (g)

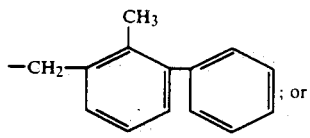 ; or  (h)

4-(4-trifluoromethyl-2-pyridyloxy)benzyl.  (j)

(j) 4-(4-trifluoromethyl-2-pyridyloxy)benzyl.
provided that:

$R_1$ is not 2,3-dichlorophenyl, 2,6-difluorophenyl, 2,6-di($C_2$-$C_4$ alkyl)phenyl, 2,4,6-tribromophenyl or 2,4,6-tri($C_1$-$C_4$ alkoxy)phenyl.

A more preferred class of compounds are those in which $R_1$ does not contain substituents at both ortho positions on the phenyl ring, i.e., in which $R_1$ does not contain a 2,6-disubstitution, 2,3,6-trisubstitution, or a 2,4,6-trisubstitution on the phenyl ring.

An even more preferred class is that in which the phenyl ring of $R_1$ is substituted at the 3-, 4-, and/or 5-positions, including mono-, di- and tri-substituted phenyl compounds, as well as phenyl compounds having a 3,4-alkylene, alkyleneoxy, perhaloalkyleneoxy, alkylenedioxy, or haloalkylenedioxy substitution. Such compounds more particularly have the formula

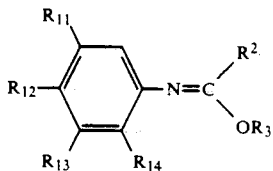

in which $R_2$ and $R_3$ are as defined about; $R_{11}$ is hydrogen, halogen, $C_1$-$C_4$ alkyl, $C_1$-$C_4$ haloalkyl, $C_1$-$C_4$ alkoxy, $C_1$-$C_4$ alkylthio, $C_1$-$C_4$ haloalkoxy, $C_1$-$C_4$ haloalkylthio, $C_2$-$C_5$ carboalkoxy, $C_2$-$C_5$ alkylcarbonyl, nitro or cyano; $R_{12}$ is hydrogen, halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, nitro, cyano, $C_2$-$C_5$ alkylcarbonyl, $C_1$-$C_4$ alkylsulfonyl or $C_2$-$C_5$ carboalkoxy; and $R_{13}$ is hydrogen, halogen, $C_1$-$C_4$ haloalkyl or $C_1$-$C_4$ alkoxy, or $R_{11}$ and $R_{12}$ taken together are $C_2$-$C_4$ alkylene, $C_2$-$C_4$ alkyleneoxy, $C_1$-$C_4$ alkylenedioxy or halo-$C_1$-$C_3$ alkylenedioxy; and $R_{14}$ is hydrogen or fluoro; provided that $R_{11}$, $R_{12}$ and $R_{13}$ are not all hydrogen.

One especially preferred subclass of such compounds is that in which $R_{11}$ is as defined above, and most preferably is halogen, $C_1$-$C_4$ alkyl, $C_1$-$C_4$ haloalkyl, $C_1$-$C_4$ alkoxy or $C_1$-$C_4$ haloalkoxy; $R_{12}$ is a $C_1$-$C_2$ polyhaloalkoxy group containing at least one fluorine atom; and $R_{13}$ is hydrogen or halogen. Examples of such polyhaloalkoxy groups are difluoromethoxy, trifluoromethoxy, difluorochloromethoxy, difluorobromomethoxy, and 1,1,2,2-tetrafluoroethoxy. Preferably $R_{14}$ is hydrogen. In one such type of compound, $R_{11}$ is chloro, $R_{12}$ is trifluoromethoxy and $R_{13}$ and $R_{14}$ are both hydrogen.

Also of interest are compounds having a 2,5-, 2,3,4- or 2,4,5-substitution pattern.

As used herein, these terms have the following meanings:

"Haloalkyl", "haloalkoxy" and similar terms include groups substituted by one or more of the same or different halogens.

"Alkyleneoxy" and "alkylenedioxy" refer to linking groups having 1 or 2 oxygen atoms, respectively, and at least one carbon atom (optionally substituted) in a chain. The alkyleneoxy moieties have 1–4, preferably 2–4, carbon atoms in this chain and include, for instance, ethyleneoxy (—O—$C_2H_4$—), dihalomethyleneoxy, dihaloethyleneoxy, and the like. Alkylenedioxy moieties include methylenedioxy (—O—$CH_2$—O—), 1,2-ethylenedioxy (—O—$C_2H_4$—O—), mono- or di-halomethylenedioxy (a methylenedioxy group in which one or both hydrogens are replaced by a halogen) and isopropylenedioxy (—O—C($CH_3$)$_2$—O—).

The term "carboalkoxy" refers to a group having the formula

in which $R_{15}$ is an alkyl group. The carbon atom content of the carboalkoxy group is meant to include the carbon atom of the carbonyl moiety in that group. Thus, $C_2$-carboalkoxy refers to carbomethoxy, etc. Similarly, the carbon atom content of an alkylcarbonyl group includes the carbon atom in the carbonyl moiety. The simplest member of this group is thus acetyl, $CH_3C(O)$—.

When $R_1$ represents a phenyl ring substituted by a second phenyl ring, the second phenyl ring may be unsubstituted or mono-substituted in which the substituent is halogen, $C_1$-$C_4$ alkyl, $C_1$-$C_4$ haloalkyl, nitro, cyano, $C_1$-$C_4$ alkylsulfonyl, $C_1$-$C_4$ haloalkylsulfonyl, or $C_1$-$C_4$ alkylenedioxy (optionally further substituted by up to 2 halogens).

Terms defining halogenated groups such as "haloalkyl", "haloalkoxy", "haloalkenyl", "haloalkenoxy" and the like include mono- and polyhalogenated groups of the indicated number of carbon atoms. In polyhalogenated groups the halogens may be the same or different.

For the various subgroups falling within the general definition of $R_3$, preferred types are:

For $R_4$: hydrogen and 2-,4- or 6-monohalo, particularly monochloro or monofluoro;

For $R_5$: 2-,3- or 4-halo, 2,4-, 3,4- or 3,5-dihalo, particularly difluoro, pentahalo, particularly pentafluoro, 4-trifluoromethyl, 4-methyl, 4-methoxy, 4-methylthio and 4-methylsulfonyl.

The following are examples of specific embodiments of groups falling within the definition of $R_3$. For convenience in specifying positions of substitution of compounds of the type

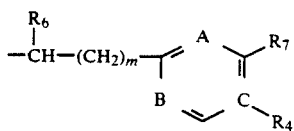

the position of attachment of the group

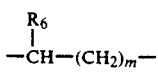

was given the number 1 and the position of attachment of group $R_7$, the number 3. When A, B or C was a nitrogen atom, the compounds were designated pyrid-2-yl, pyrid-6-yl or pyrid-4-yl, respectively.
3-phenoxybenzyl,
3-phenoxy-(alpha-methyl)benzyl,
3-phenoxyphenethyl,
3-(4-pyridyloxy)benzyl,
3(4-fluorophenoxy)benzyl,
3-(4-chlorophenoxy)benzyl,
3-(4-bromophenoxy)benzyl,
3-(4-iodophenoxy)benzyl,
3-(2,4-difluorophenoxy)benzyl,
3-(2,4-difluorophenoxy)benzyl,
3-(3,5-difluorophenoxy)benzyl,
3-(2,3,4,5,6-pentafluorophenoxy)benzyl,
3-(4-fluorophenoxy)-4-fluorobenzyl,
3-(4-fluorophenoxy)-4-chlorobenzyl,
3-(4-chlorophenoxy)-4-fluorobenzyl,
3-phenoxy-4-fluorobenzyl,
3-(4-fluorophenoxy)-6-chlorobenzyl,
3-(4-fluorophenoxy)-5-fluorobenzyl,
3-(4-fluorophenoxy)-4,6-difluorobenzyl,
3-(4-methylphenoxy)benzyl,
3-(4-methoxyphenoxy)benzyl,
3-(3,4-difluorophenoxy)-4-fluorobenzyl,
3-(3-fluorophenoxy)benzyl,
3-(2-fluorophenoxy)benzyl,
3-(3-chlorophenoxy)benzyl,
3-(4-trifluoromethylphenoxy)benzyl,
3-(4-methylthiophenoxy)benzyl,
3-(4-fluorophenoxy)-(alpha-fluoro)benzyl,
3-phenoxy-pyrid-2-yl methyl,
3-phenoxy-pyrid-4-yl methyl,
3-phenoxy-pyrid-6-yl methyl,
3-(4-methylphenoxy)pyrid-2-ylmethyl,
3-(4-fluorophenoxy)pyrid-2-ylmethyl,
3-(4-chlorophenoxy)pyrid-2-ylmethyl,
3-(4-fluorophenoxy)pyrid-4-ylmethyl,
3-(4-chlorophenoxy)pyrid-2-ylmethyl,
3-(4-chlorophenoxy)pyrid-4-yl-methyl,
3-(4-chlorophenoxy)pyrid-6-yl-methyl,
3-(3,4-difluorophenoxy)pyrid-2-methyl,
3-(pyrid-2-yloxy)benzyl,
3-(4-chloropyrid-2-yloxy)benzyl,
2,3,4,5,6-tetrafluorobenzyl,
4-methoxymethyl-2,3,5,6-tetrafluorobenzyl,
4-propargyl-2,3,5,6-tetrafluorobenzyl,
3-allyloxybenzyl,
3-(benzyl)benzyl,
3-(benzyloxy)benzyl,
3-(4-fluorobenzyloxy)benzyl,
3-(phenylamino)benzyl,
3-(4-fluorophenylamino)benzyl,
2-methyl-3-phenylbenzyl,
1-(3-phenoxyphenyl)prop-2-ynyl,
3-bromo-4-fluorobenzyl,
4-phenoxy-2-butyn-2-yl,
4-(benzyloxy)benzyl,
4-(4-fluorobenzyloxy)benzyl,
4-(4-trifluoromethyl-2-pyridyloxy)benzyl,
5-benzyl-3-furanylmethyl.

Processes for Preparation of Compounds of This Invention Process (A)

Compounds of this invention in general are prepared by reaction of an imidoyl halide (preferably chloride) with an alkali metal alkoxide according to the general reaction:

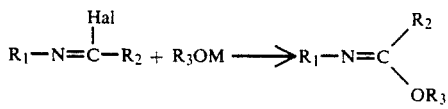

in which M is an alkali metal, preferably sodium or potassium and Hal is a halogen, particularly chloro or bromo.

This reaction is conducted at a temperature of from about $-70°$ C. to about $+65°$ C., most preferably at about room temperature, for a time which may range from about 5 minutes to about 24 hours. The reaction is conducted in the presence of a solvent, for example, an aromatic hydrocarbon such as benzene, toluene, or xylene, or an ether, such as diethyl ether, diisopropyl ether, diisoamyl ether, dibutyl ether, furan, 1,3-dimethoxyethane, or tetrahydrofuran (preferably tetrahydrofuran). In some instances, apparent to those skilled in the art, it is advantageous to add the solution of the alkali metal alkoxide to a solution of the imidoyl halide or to use substantial excesses of alkoxide. The resulting product may be recovered by conventional techniques.

The alkoxide $R_3OM$ is produced by reaction of an appropriate alcohol, such as 3-phenoxybenzyl alcohol, with an alkali metal-containing base, for instance, an alkali metal hydride (e.g., potassium or preferably sodium hydride) in the presence of a solvent such as that used in reaction of the alkali metal alkoxide with the imidoyl halide. In general, this reaction is conducted at reflux temperature under an inert atmosphere for a time which may range up to about 2 hours.

The alcohols, if not commercially available, can be prepared according to known methods such as those described in the following references: U.S. Pat. Nos. 4,256,893, 4,261,920, and 4,329,518; and Volume 7 of the test "Chemie der Pflanzenschutz und Schadlingsbekampfungsmittel" (phenoxybenzyl, phenoxypyridyl and pyridyloxybenzyl type alcohols); Elliott et al., J. Chem. Soc. (C), 1971, pp 2551-1554 (5-benzyl-2-furanylmethanol), Pesticide Science 14, 560-570 (1983) (2-methyl-3-phenylbenzyl alcohol); U.S. Pat. No. 4,594,355; British patent No. 2,122,616; U.S. Pat. No. 4,370,346; European patent applications Nos. 196,156 and 271,240; and J. Sci. Food & Agriculture, 18, 167 (1967) for various substituted benzyl alcohols; European patent application 211,561 for 3-phenylaminobenzyl alcohols; Swiss patent No. 549,342 for 4-phenoxy-2-butyn-1-ol; and Japanese patent No. 49-27331 for 1-(3-phenoxyphenyl)-2propyn-1-ol.

The imidoyl halide may be prepared from a starting amine having the formula $R_1NH_2$ or amide having the formula

depending on availability. The amines are either generally available or may be prepared by procedures known in the art; for example, those described in "Compendium of Organic Synthetic Methods", Harrison et al. (Wiley-Interscience, N.Y., 1971).

The amides, if not available, may be produced by reaction of the amine with an appropriate acid chloride having the formula

The temperature of this reaction ranges from about $-40°$ C. to about $+80°$ C. Suitable solvents include hydrocarbon solvents such as toluene and chlorinated hydrocarbon solvents such as methylene chloride, chloroform, carbon tetrachloride, ethylene dichloride, tetrachloroethane and the like, preferably methylene chloride. This reaction is conducted in the presence of a base, preferably a tertiary amine. Suitable bases include triethylamine, quinoline, dimethylaniline, diethylaniline, and pyridine. Triethylamine is the preferred base. The resulting amide is recovered and purified by conventional means.

The imidoyl halide may be prepared from the amide by reacting it with a halogenating agent such as phosphorus pentachloride or phosgene in an organic solvent such as that utilized in the amide production (preferably methylene chloride) or alternatively using phosphorus oxychloride as the solvent. The reaction is carried out under an inert atmosphere for a time which may be up to 24 hours, preferably from 1 to 24 hours, at a temperature of from about $0°$ C. to about $110°$ C. Before the imidoyl chloride-containing product is passed to the final step, all substances, such as phosphorus oxychloride or hydrogen chloride, which can react with the alkoxide in the final step, should be removed. This can generally be accomplished by evaporation or distillation.

Alternatively, the compounds of this invention may be prepared by a two-step process indicated as follows:

Process (B)

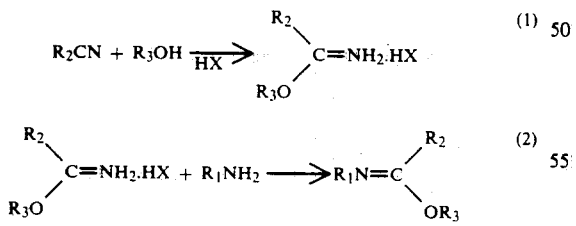

in which "HX" represents a mineral acid.

In the first step, the appropriate alcohol (for instance a phenoxybenzyl alcohol) is mixed with a nitrile having the formula $R_2CN$ at a temperature of from about $-20°$ C. to about $+40°$ C. Then, a solution of a mineral acid such a hydrochloric, hydrobromic, sulfuric or phosphoric acid (preferably hydrochloric acid) dissolved in a suitable organic solvent is added at temperatures from about $-5°$ to about $40°$ C., preferably $0°$ C., then stirred at room temperature, to produce the corresponding imidate salt. Suitable solvents for this reaction include aromatic hydrocarbons such as benzene, toluene, or xylene and ethers such as diethyl ether, diisopropyl ether, diamyl ether, furan, tetrahydrofuran and dioxane (preferably dioxane). Time for the reaction may be up to 52 hours. The imidate salts are novel and constitute an aspect of this invention.

In the second step, the imidate salt is suspended in an organic solvent such as that utilized in the previous step, preferably benzene, and reacted with an amine having the formula $R_1NJ_2$. The mixture is reacted, optionally with stirring, at a temperature of between about $-50°$ and $+80°$ C., most preferably at room temperature, for a period of time necessary to conduct the reaction, which may be up to 120 hours. The final imidate product may be recovered as in process (A).

Process (C)

A third process may be used for producing the compounds of this invention. This process proceeds by way of an intermediate ketenimine, which may be prepared from the amide or from the imidoyl halide. In the first case, the amide (prepared for instance, as described in process (A) is reacted with an inexpensive base and a trivalent phosphorus compound, preferably triphenylphosphine. The base is preferably a tertiary amine such a triethylamine. The reaction is carried out at a temperature of from about $-10°$ C. to $40°$ C. in the presence of a halogen, preferably chlorine or bromine, and an aromatic or chlorinated hydrocarbon solvent such as benzene, toluene, xylene, methylene chloride, ethylene dichloride, chloroform, carbon tetrachloride, tetrachloroethane and the like, preferably methylene chloride. The reaction may then be conducted under reflux temperature of the solvent and the ketenimine recovered according to methods known in the art.

Alternatively, the ketenimine may be prepared by reaction of the imidoyl halide with a base, as just described, but no halogen or trivalent phosphorus compound present.

In the second step of this process, the ketenimine is reacted with an alcohol having the formula $R_3OH$ in the presence of a solvent, preferably an ether solvent, such a diethyl ether, dipropyl ether, diisopropyl ether, dibutyl ether, tetrahydrofuran or 1,2-dimethoxyethane and an alkali metal base such as potassium or sodium hydride, preferably sodium hydride. This reaction is conducted under reflux for a time as necessary which may be up to 48 hours, preferably from about 2 to about 10 hours, at the end of which the reaction mixture is cooled and the imidate product recovered as described above.

This process can be depicted by the general scheme:

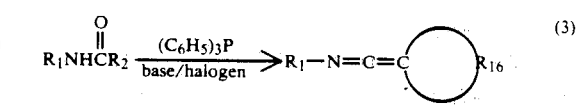

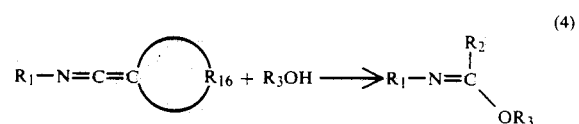

in which R₁, R₂ and R₃ are as previously described and R₁₆ is a 1,2-ethylene group optionally substituted by up to 4 methyl groups or up to 2 halogens.

Ketenimines

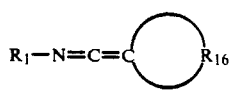

are novel.

Process (D)

This process may be used as an alternative to Process (A) for preparation of compounds of this invention from alcohols (R₃OH) which are sensitive to, and could be adversely affected (e.g. decomposed) by, strong bases such as the alkali metal-containing bases (e.g. alkali metal hydrides) used to prepare the alkoxides (R₃OM). Alcohols which may be sensitive to such strong bases include phenoxypyridyl alkanols, alpha-ethynyl alcohols (R₆is ethynyl) such as 1-(3-phenoxyphenyl)-2-propyn-1-ol and tetrafluoropropargylbenzyl alcohol.

Compounds of this type may be made by direct reaction of the alcohol with the imidoyl chloride in the presence of a tertiary amine base and a reaction-promoting amount of a 4-di(lower alkyl)aminopyridine, preferably 4-dimethylaminopyridine.

Tertiary amines which may be used in this process include trialkylamines such as trimethyl-, triethyl-, tri-n-butylamine and the like, including tertiary amines having mixed alkyl groups, N,N-dialkylanilines such as N,N-dimethylaniline, pyridine and various substituted pyridines. Preferred tertiary amines, primarily for economic reasons, are triethylamine, N,N-dimethylaniline and pyridine. The tertiary amine may even be an additional amount of the promoter 4-di(lower alkyl)aminopyridine, over and above that amount needed for promoting the reaction.

The tertiary amine is preferably used in a stoichiometric amount with respect to the alcohol, but may be used in excess of that amount. The promotor 4-di(lower alkyl)aminopyridine may be used in an amount from about 0.05 to about 1 equivalent per equivalent of alcohol, preferably from about 0.05 to about 0.15 equivalent per equivalent, most preferably about 0.1.

This process is preferably conducted at temperatures of from about 20° C. to about 50° C. Lower temperatures may be used, but the reaction rate would be much slower. The process is carried out in the presence of an inert solvent such as an aromatic hydrocarbon (for instance, benzene, toluene or xylene), chlorinated solvent (such as methylene chloride, ethylene dichloride or chlorobenzene) or an ether (such as diethyl ether, dioxane or tetrahydrofuran).

While this process is particularly suitable for producing compounds from base-sensitive alcohols, it may be used to produce compounds of this invention in general from other alcohols as described.

Alpha-fluorophenoxybenzyl compounds are made from the alphafluorobenzyl halide (preferably bromide) rather than the alcohol by reaction with an amide, R₁NHCOR₂, in the presence of a halide ion binding agent such as silver oxide or a silver salt, and an inert solvent. Reaction temperatures are from about −20° C. to about 100° C.

The following is a representative example of the preparation of compounds of this invention.

Preparation of N-(4-Chlorophenyl)-O-(3-phenoxybenzyl)cyclopropylcarboximidate (Compound 4 herein) (Process A)

N-(4-chlorophenyl)cyclopropane carboxamide (4.0 g, 20.4 mmol), prepared from 4-chloroaniline and cyclopropane carboxylic acid chloride analogously to Example 1, step (a) was dissolved in 50 ml methylene chloride and treated with PCl₅ (14.25 g, 20.4 mmol) all at once, under an argon atmosphere. After 20 minutes, n-pentane was added and the solid was filtered. The solvents were evaporated at 50° C., yielding a residual light brown oil, the desired imidoyl chloride. This was taken up in a small amount of dry tetrahydrofuran.

The imidoyl chloride thus prepared was then added to a solution of sodium 3-phenoxybenzyl alkoxide prepared using 4.1 g of 3-phenoxybenzyl alcohol and 0.5 g of sodium hydride as in Example 1, step (c). The mixture was let stand for 4 hours at room temperature then briefly heated to reflux and cooled. WAter and hexanes were added and the aqueous and organic phases separated. The organic layer was washed with water, dried over magnesium sulfate and evaporated. The residue was redissolved in hexanes and filtered through silica gel. Evaporation gave a colorless oil, identified spectroscopically as the desired product.

The following Table 1 depicts representative compounds of this invention, prepared according to a method as described above. Nearly all the compounds were produced as oils. The structures of the compounds in Table 1 were confirmed by spectroscopic analyses.

TABLE 1

| Compound No. | R₁ | R₂ | R₃ |
|---|---|---|---|
| 1 | Cl—C₆H₄— | CH₃-cyclopropyl | —CH₂—C₆H₄—O—C₆H₅ |
| 2 | Cl—C₆H₄— | cyclopropyl-CH₃ | —CH₂—C₆H₄—O—C₆H₅ |

TABLE 1-continued

| Compound No. | R₁ | R₂ | R₃ |
|---|---|---|---|
| 3 | 3-Cl-phenyl | cyclopropyl | -CH₂-(3-phenoxyphenyl) |
| 4 | 4-Cl-phenyl | cyclopropyl | -CH₂-(3-phenoxyphenyl) |
| 5 | 4-F-phenyl | cyclopropyl | -CH₂-(3-phenoxyphenyl) |
| 6 | 4-CF₃-phenyl | cyclopropyl | -CH₂-(3-phenoxyphenyl) |
| 7 | 4-CF₃O-phenyl | cyclopropyl | -CH₂-(3-phenoxyphenyl) |
| 8 | 3-Cl-4-CF₃-phenyl | cyclopropyl | -CH₂-(3-phenoxyphenyl) |
| 9 | 3-CF₃-phenyl | cyclopropyl | -CH₂-(3-phenoxyphenyl) |
| 10 | 3-Cl-4-F-phenyl | cyclopropyl | -CH₂-(3-phenoxyphenyl) |
| 11 | 3-Cl-4-F-phenyl | cyclopropyl | -CH₂-[3-(4-fluorophenoxy)phenyl] |
| 12 | 3-Cl-4-F-phenyl | 2,2,3,3-tetramethylcyclopropyl | -CH₂-(3-phenoxyphenyl) |
| 13 | 3,4-methylenedioxyphenyl | cyclopropyl | -CH₂-(3-phenoxyphenyl) |

TABLE 1-continued

| Compound No. | R₁ | R₂ | R₃ |
|---|---|---|---|
| 14 | 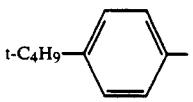 |  | 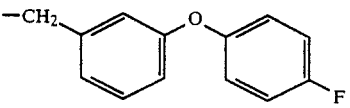 |
| 15 | 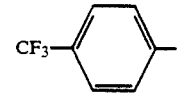 |  | 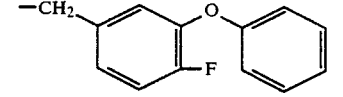 |
| 16 | 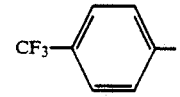 |  | 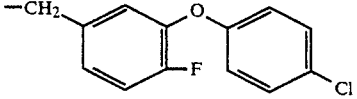 |

Insecticidal Evaluation Tests

The compounds in Table 1 above were tested for insecticidal activity using the following testing procedures. LC₅₀ values, based on the results of these tests and calculated according to dosage-mortality curves, are expressed in Table 2.

Housefly [*Musca domestica*]

The test compound was diluted in acetone and aliquots pipetted onto the bottom of aluminum dishes. To ensure even spreading of the chemical on the bottom of the dishes, 1 ml of acetone containing 0.01% peanut oil was also added to each dish. After all solvents had evaporated, the dishes were placed in circular cardboard cages containing 25 female houseflies, 1-2 days old. The cages were covered on the bottom with cellophane and on the top with tulle netting, and each contained a sugar-water saturated cotton plug for maintenance of the flies. Mortality was recorded after 48 hours. Test levels ranged from 100 µg/25 female houseflies downward. The LC-50 value is expressed below in Table 2 under the heading "HF", in terms of µg of the test compound per 25 female flies.

Black Bean Aphid [*Aphis fabae* (Scop.)]

Nasturtium plants (Tropaeolum sp.) approximately 5 cm tall, were transplanted into sandy loam soil in small cups and infested with 25-50 black bean aphids of mixed ages. Twenty-four hours later they were sprayed to the point of runoff with 50—50 acetone-water solutions of the test compound. Treated plants were held in the greenhouse and mortality was recorded after 48 hours. Test concentrations ranged from 0.05% downward. The LC-50 value is expressed below in Table 2 under the heading "BBA" in terms of percent of the test compound in the sprayed solution.

Tobacco Budworm [*Heliothis virescens* (Fabricius)]

(a) Contact: Test compounds were diluted in a 50—50 acetonewater solution. Cotton (Gossypium sp.) cotyledons were immersed in the test solutions for 2-3 seconds and placed on a wire screen to dry. The dried leaves were placed in petri dishes containing a moistened piece of filter paper and infested with 5 secondinstar tobacco budworm larvae. The dishes were placed in a high humidity chamber for 5 days, and percent mortality of the larvae recorded. Test concentrations ranged from 0.1% downward. The LC-50 values are expressed below in Table 2 under the heading "TBW-C" in terms of percent of the test compound in the solution.

(b). Eggs: Paper towel patches of 2-day old eggs of the tobacco budworm were dipped in acetone solutions of the test compound and placed in petri dishes containing a portion of larval rearing medium. Treated eggs were maintained at 78° F. and mortality was recorded after all control eggs had hatched and the young larvae were feeding on the media. Test concentrations ranged from 0.1% downward. The LC-50 value is expressed below in Table 2 under the heading "TBW-E" in terms of percent of the test compound in the solution.

Cabbage Looper [*Trichoplusia ni* (Hubner)]

The test compound was diluted in a 50—50 acetone-water solution. Cotyledons of hyzini squash (*Calabacita abobrinha*), approximately 1×1.5 inches, were immersed in the test solutions for 2-3 seconds and placed on a wire screen to dry. The dried leaves were placed in petri dished containing a moistened piece of filter paper and infested with 5 secondinstar cabbage looper larvae. The dished were placed in a high humidity chamber. Mortality of the larvae was recorded 3-5 days later. Test concentrations ranged from 0.1% downward. The LC-50 value is expressed below in Table 2 under the heading "CL" in terms of percent of the test compound in solution.

Beet Armyworm (*Spodoptera exigua*)

Test compounds were diluted in a 50—50 acetone-water solution. Young leaves of sugar beets (*Beta vulgaris*) were immersed in the test solutions for 2-3 seconds and placed on a wire screen to dry. The dried leaves were placed in petri dishes containing a moistened filter paper and infested with five second-instar beet armyworm larvae. The dishes were placed in a high humidity chamber. Mortality of the larvae was recorded five days later. Test concentrations ranged from 0.1% downward. The LC-50 values are expressed below in Table 2 under the heading "BAW" in terms of percent of the test compound in solution.

Western Spotted Cucumber Beetle Larvae[*Diabrotica undecimpunctata undecimpunctata* (Mannherheim)]

Ten grams of moist potting soil was placed in a plastic cup. The test compound was dissolved in acetone. A 0.05 ml aliquot of the test sample, diluted to the desired concentration, was added to the soil. The cup was capped and the soil was mixed on a vortex mixer for approximately 15 seconds. An indentation was made on the surface of the soil and approximately 50 Diabrotica eggs were added. The eggs were covered with soil and maintained at room temperature (approximately 70° F. or 21° C.). Four days later a section of Romaine lettuce (*Latuca sativa*) leaf was placed in the treated cups. One week later the cups were examined for live larvae. TEst concentrations ranged from 25 ppm downward. The LC-50 value is expressed below in Table 2 under the heading "Diabrotica" in terms of ppm of the test compound in the soil.

in 50—50 acetone-water solutions of the test compound. Treated plants were held in the greenhouse, and 5-7 days later mortality was determined for both adult mites and the nymphs hatching from eggs which were on the plants at the time of treatment. Test concentrations ranged from 0.05% downward. The LC-50 value is expressed below in Table 2 under the headings "2SM-A" (i.e., adults) and "2SM-E" (i.e. eggs) in terms of percent concentration of the test compound in the solution.

TABLE 2

| Cmpd. No. | HF µg | BBA % | 2-SM A/% | 2-SM E/% | (LC$_{50}$) TBW, % C | TBW, % E | BAW % | CL % | Diabrotica ppm (soil) | LH% |
|---|---|---|---|---|---|---|---|---|---|---|
| 1 | 21 | 0.001 | >0.05 | >0.05 | 0.008 | 0.05 | 0.025 | 0.005 | >25 | >0.05 |
| 2 | >100 | >0.05 | >0.05 | >0.05 | — | >0.01 | — | 0.025 | >25 | — |
| 3 | 25 | 0.01 | >0.05 | >0.05 | — | 0.1 | — | 0.005 | >25 | — |
| 4 | 37 | 0.003 | 0.01 | 0.05 | 0.006 | 0.1 | 0.03 | 0.003 | >25 | >0.05 |
| 5 | 30 | 0.03 | 0.05 | 0.05 | 0.01 | 0.08 | 0.1 | 0.03 | >25 | >0.05 |
| 6 | 20 | 0.001 | 0.01 | >0.05 | 0.0015 | 0.025 | 0.02 | 0.005 | 25 | — |
| 7 | 30 | 0.0003 | 0.01 | 0.01 | 0.001 | 0.05 | 0.005 | 0.005 | 17 | 0.0001 |
| 8 | >100 | >0.05 | >0.05 | >0.05 | 0.1 | >0.1 | >0.1 | <0.01 | 25 | — |
| 9 | 65 | >0.05 | >0.05 | >0.05 | — | >0.1 | — | 0.013 | >25 | — |
| 10 | 15 | — | >0.05 | >0.05 | — | 0.1 | — | 0.005 | >25 | — |
| 11 | 15 | — | >0.05 | >0.05 | — | 0.05 | >0.1 | 0.00025 | >25 | — |
| 12 | 17 | >0.05 | 0.05 | 0.05 | — | >0.01 | — | 0.01 | >25 | >0.05 |
| 13 | 13 | 0.01 | >0.05 | >0.05 | — | >0.01 | — | 0.002 | >25 | — |
| 14 | >100 | — | 0.02 | 0.02 | — | >0.1 | — | 0.017 | >25 | >0.05 |
| 15 | <100 | 0.0003 | <0.05 | <0.05 | — | 0.017 | — | 0.00015 | >25 | — |
| 16 | >100 | 0.0006 | >0.05 | >0.05 | — | 0.023 | — | 0.00015 | >25 | — |

Contact Residue Assay on the Aster Leafhopper [*Macrosteles fascifrens* (Stal)]

Oat seedlings (Avena sp) were grown in a commercial potting soil in cups. When the plants were approximately 10 cm tall they were thinned to three plants per cup and dipped for 2-3 seconds in 50—50 acetone-water solutions of the test compounds. When the plants had dried, a clear plastic tube was placed over them and the bottom end pressed into the cup. Ten aster leafhopper adults/nymphs were then placed in each tube and the tops of the tubes covered with white organdy cloth. Mortality counts were made after 48 hours. Test concentrations ranged from 0.05% down to that at which 50% mortality occurred. The LC$_{50}$ values are expressed below in Table 2 under the heading "LH" in terms of the percent of the test compound in the solution.

Maize weevil (*Sitophilus zeamais* [Motschulsky])

Test compounds were diluted in a 50:50 acetone:water solution to a concentration of 0.01%. Four corn seeds [*Zea mays*, (L.)] which had been immersed in test solutions for 2-3 seconds and allowed to dry were placed in covered containers at a temperature of about 25° C. Mortality was recorded after 48 hours. Of seven compounds in Table 1 so tested, only Compounds 13 and 15 showed 50% mortality.

Acaricidal Evaluation Test

The two-spotted mite (2SM) [*Tetranychus urticae* (Koch)] was employed in tests for miticides. The test procedure was as follows:

Pinto bean plants (Phaseolus sp.), approximately 10 cm tall, were transplanted into sandy loam soil in small cups and thoroughly infested with two-spotted mites of mixed ages and sexes. Twenty-four hours later the infested plants were inverted and dipped for 2-3 seconds The insecticidal activity, and therefore the inclusion of a compound not mentioned specifically herein within the class of compounds of this invention, as determined by general formula (I), may be determined by evaluating such a compound using one or more of the above-described procedures. If a test compound demonstrates activity against one or more of the insects mentioned, by virtue of causing 50 percent or greater mortality at the initial evaluation level, it is considered "insecticidal" for the purposes of this invention.

In practice a pure compound (active compound) can be used as an insecticide. However, in general, the compounds are first formulated with one or more inert (i.e. non-chemically reactive, plant compatible or herbicidally inert) carriers or diluents suitable for insecticidal use, before being applied.

The compositions or formulations, including a compound as described herein, may take any one of a number of solid or liquid forms. Examples of solid forms are dusts, granules, tablets, powders and the like. Examples of liquid forms are emulsions, solutions, suspensions, flowables, emulsifiable concentrates and pastes. Such compositions may contain, in addition to the active compound or compounds, various carriers or diluents; surface-active agents (wetting agents, dispersing agents and/ or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcined diatomaceous earth, calcium carbonate, silica, kieselguhr, clays, etc.; ground synthetic minerals such a various silicates and alumino-silicates and ground vegetable products such as bark, cornmeal, sawdust, cellulose powder and the like. Compositions containing sorptive clays will usually also contain a stabilizer, such as a glycol, to prevent or minimize degradation of the active ingredient.

To manufacture solid compositions, the active compounds are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents may also be added.

Flowables are prepared by mixing an active compound with one or more dispersing agents and/or solid additives, and a liquid (which may be water or an organic solvent) in which the active compound is relatively insoluble, and grinding the mixture.

Both liquid and solid compositions may be in microcapsule or encapsulated form, to permit release of the enclosed active compound at a controlled rate over a period of time. Liquid compositions of this type contain encapsulated droplets of approximately 1-50 microns in diameter, including the active compound and optionally a solvent. The encapsulating material is an inert porous membrane of a polymeric material.

Solid encapsulated compositions generally take the form of granules, in which the liquid containing the active component is trapped in the pores of the granular support by a porous polymeric membrane through which the active ingredient may migrate at a controlled rate, or which membrane breaks down at a controlled rate to permit escape of the active ingredient.

Typical encapsulating materials include natural and synthetic rubbers, cellulosic materials, styrene-butadiene copolymers, polyacrylonitriles, polyacrylates, polyamides, polyisocyanates, polyurethanes, mixed copolymers of the foregoing and starch xanthates.

It is possible to use highly concentrated liquid compositions containing up to about 95% by weight of the active compound, or even the 100% active compound alone, when applying the compound in the form of a finely divided liquid by use of various atomizing equipment, for example by airplane spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound; oil suspensions, emulsions, solutions, flowables, and emulsifiable concentrates: 5 to 85% active compound; aqueous suspensions: 20 to 50% active compound; dusts and powders: 5 to 20% active compound; granules and pellets: 5 to 20% active compound.

In addition to the active compound and the various agents utilized in preparing compositions and formulations mentioned, such compositions may also contain one or more other active compounds of the type mentioned herein, as well as other active pesticidal agents such as herbicides, fungicides, insecticides, acaricides, nematocides, bactericides, and plant growth regulators. The particular pesticide included in the mixture will depend upon its intended utility and the type of complementary action required. Examples of suitable insecticides include the following:

(a) natural pyrethrins or pyrethroids such as permethrin, esfenvalerate, deltamethrin, cyhalothrin, biphenthrin, fenpropathrin, cyfluthrin, tefluthrin, empenthrin, ethofenprox, tetramethrin, bioallethrin, fenfluthrin, prallethrin, 5-benzyl- 3-furylmethyl-(E)-(1R,3S)-2,2-dimethyl-3(2-oxothiolan-3-ylidene-methyl)cyclopropane carboxylate, and pentafluorobenzyl (cis)-3-[2-fluoro-2-(methoxycarbonyl)ethenyl]2,2-dimethylcyclopropane carboxylate;

(b) organophosphates such as profenofos, sulprofos, phosmet, dichlorvos, methyl parathion, azinphosmethyl, dimeton-s-methyl, heptenophos, thiometon, fenamiphos, monocrotophos, triazophos, methamidophos, dimethoate, phosphamidon, malathion, chlorpyrifos, phosalone, fensulfothion, fonofos, phorate, phoxim, pyrimiphosmethyl, fenitrothion and diazinon;

(c) carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) benzoyl ureas such as triflumurom, chlorofluazuron;

(e) organic tin compounds such as cyhexatin, fenbutatin oxide, azocyclotin;

(f) macrolides such as avermectins or milbemycins, for example such as abamectin, avermectin, and milbemycin;

(g) hormones and synthetic mimics thereof such as juvenile hormone, juvabione, ecdysones, methoprene and hydroprene;

(h) pheromones; and (i) organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofesin, can be employed. Alternatively, insecticides specific for particular insect species/stages, for example ovolarvicides such as clofentezine, amitraz, chlordimeform flubenzimine, hexythiazox and tetradifon, motilicides such as dicofol or propargite, adulticides such as bromopropylate, chlorobenzilate, or insect growth regulators such as hydramethylon, cyromazine, methoprene, chlorofluazuron and diflubenzuron may also be included in the compositions. Such compositions may also contain soil disinfectants or fumigants and may further contain fertilizers, thus making it possible to provide multi-purpose compositions containing one or more of the active compounds described herein as well as, optionally, other pesticides and also fertilizers, all intended and formulated for use at the same locus.

Control of insect pests is accomplished by applying a composition containing an insecticidally effective amount of an active compound as described herein to the insect, to a locus at which insecticidal control is desired, or to food sources (including seeds) on which the insects feed. For use in the last mentioned manner it is preferable to utilize a compound which is not volatile. Thus, control may be achieved by direct application of the active compounds to the insects and indirectly by application of the compounds to a locus to be protected (such as crop lands, grass ranges and forests), to a source of food for insects or to other insect habitats (for example, breeding or swarming areas). The rates of application of the active compound and the concentration applied will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.011 to about 111 kg/ha).

It should be noted that the active compound need not be insecticidally active per se to effect insect control. The purposes of this invention are fully served if such compounds are rendered active by external influences, such a light or heat, or by some physiological action which occurs when the compound is ingested into the body of the insect.

Compounds of this invention could be used to control a variety of insects such as:
*Myzus persicae* (aphid)
*Aphis gossypii* (aphid)
*Aphis fabae* (aphid)
*Megoura viceae* (aphid)
*Aedes aegypti* (mosquito)
Anopheles spp. (mosquitoes)
Culex spp. (mosquitoes)
*Dysdercus fasciatus* (capsid)
*Musca domestica* (housefly)
*Pieris brassicae* (white butterfly)
*Plutella maculipennis* (diamond back moth)
*Phaedon cochlaeriae* (mustard beetle)
Aonidiella spp. (scale insects)
Trialeuroides spp. (white flies)
*Bemisia tabaci* (white fly)
*Blattella germanica* (cockroach)
*Periplaneta americana* (cockroach)
*Blatta orientalis* (cockroach)
*Spodoptera littoralis* (cotton leafworm)
*Heliothios virescens* (tobacco budworm)
*Chortiocetes terminifera* (locust)
Diabrotica spp. (rootworms)
Agrotis spp. (cutworms)
*Chilo suppressalis* (stem borer)
*Chilo partellus* (maize stem borer)
*Nilaparvata lugens* (planthopper)
*Nephottex virescens* (leafhopper)
*Nephotettix cincticeps* (leafhopper)
*Panonychus ulmi* (European red mite)
*Panonychus citri* (citrus red mite)
*Tetranychus urticae* (two-spotted spider mite)
*Tetranychus cinnabarinus* (carmine spider mite)
*Phyllcoptruta oleivora* (citrus rust mite)
*Polyphagotarsonemus latus* (broad mite)
Brevipalpus spp. (mites)

Compositions containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (i.e., after infestation). Thus, powders and various liquid compositions containing the active compound can be applied by the use of power dusters, boom and hand sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions including active compounds may additionally be used to protect plant seeds from being attacked by soil-borne insect pests after panting and during germination, by applying the composition to the seeds as a seed dressing. This is performed generally by mixing the seeds with an active composition in either liquid or solid form (preferably liquid) in a suitable mixing apparatus. Liquid compositions for this purpose may contain an adhesive or sticking agent, such as methyl cellulose, ethyl cellulose, etc., to assist the composition in adhering to the seed. If a solid composition is utilized for this purpose, an adhesive agent may be sprayed on the seeds during or after mixing.

For use as a soil insecticide, the active compound, or compositions containing it, may be mixed with the soil in any conventional manner, before, during or after planting of the plant seeds. Liquid compositions may be applied by spraying onto the surface or by incorporation in irrigation or sprayed water. Solid or liquid compositions containing an active compound may be incorporated into the soil prior to or during planting by discing, plowing or other mixing operations, in order to locate the active ingredient below the surface of the soil so as to be most effective in controlling undesirable larvae.

Some examples of compositions containing the active compounds of this invention are:

| Component | | Weight % |
|---|---|---|
| Composition A: Granular Solid | | |
| Active compound | | 10 |
| attapulgite clay granules | | 85 |
| triethylene glycol | | 5 |
| | Total | 100% |
| Composition B: Wettable Powder | | |
| Active compound | | 80 |
| wetting agent (sodium dialkyl-naphthalene sulfonate) | | 1 |
| dispersing agent (sodium lignosulfonate) | | 4 |
| diluent (aluminum magnesium silicate) | | 15 |
| | Total | 100% |
| Composition C: Dilute Solution | | |
| Active compound | | 5 |
| solvent (xylene) | | 95 |
| | Total | 100% |
| Composition D: Emulsifiable Concentrate | | |
| Active compound | | 50 |
| Emulsifier (blend of metal sulfonates and polyoxyethylene ethers) | | 10 |
| solvent (xylene) | | 40 |
| | Total | 100% |

| Component | Weight % |
|---|---|
| Composition E: Concentrated Solution | |
| Active compound | 90 |
| solvent (xylene) | 10 |
| Total | 100% |

What is claimed is:

1. A compound having the formula $$R_1-N=C\begin{matrix}R_2\\\\OR_3\end{matrix} \quad (I)$$

in which $R_1$ is naphthyl, optionally substituted by up to 2 halogens; or phenyl, optionally substituted by one or more of: $C_2-C_5$ carboalkoxy, $C_1-C_4$ alkylsulfonyl, $C_1-C_4$ haloalkylsulfonyl, $C_2-C_5$ alkylcarbonyl, $C_2-C_4$ alkenyl, $C_3$-haloalkenoxy, $C_1-C_4$ haloalkylthio, $C_3-C_6$ cycloalkyl, phenyl, monosubstituted phenyl, pyridyloxy, $C_2-C_4$ alkyleneoxy, $C_1-C_4$ alkylenedioxy, $C_1-C_3$ haloalkylenedioxy, $C_2-C_4$ alkylene, amido, nitro, cyano, up to two $C_1-C_4$ alkylthio groups, up to three $C_1-C_4$ alkoxy groups, up to three $C_1-C_4$ haloalkoxy groups, up to three $C_1-C_4$ alkyl groups, up to three $C_1-C_4$ haloalkyl groups, or up to five halogens;

$R_2$ is cyclopropyl, optionally substituted by one or 4 methyl groups or up to 2 halogens; and $R_3$ is (a) —CH(R_6)—(CH_2)_m—[ring with A, B, C, R_4, R_7]

in which m is 0 or 1;

A, B and C are each carbon or nitrogen, provided that A, B and C are not all nitrogen and if two of A, B and C are nitrogen, then A and C are nitrogen;

$R_4$ is hydrogen, monohalo or dihalo;

$R_6$ is hydrogen, methyl, fluoro or ethynyl; and $R_7$ is (i) —O—[CH=CH—CH=E—R_5 group with D]

in which D and E are each carbon or nitrogen provided that both D and E are not nitrogen, and further provided that if any of A, B or C is nitrogen, then D and E are both carbon; and $R_5$ is hydrogen, $C_1-C_4$ alkyl, $C_1-C_4$ alkoxy, trifluoromethyl, cyano, $C_1-C_4$ alkylthio, $C_1-C_4$ alkylsulfonyl, or mono- or polyhalo;

(ii) —NH—[phenyl]—$R_8$;

—CH_2—[phenyl]—$R_8$;

—OCH_2—[phenyl]—$R_8$;

in which $R_8$ is hydrogen or halogen; or (iii) —O—CH_2—CH=CH_2;

(b) —CH_2—[phenyl with $R_9$ and $(R_{10})_4$]

in which (i) $R_9$ is 4-fluoro, 4-methoxymethyl, or 4-propargyl, and $R_{10}$ is fluoro or (i) $R_9$ is 3- or 4-allyl, 3- or 4-propargyl, or 3- or 4-(mono- or dihalo)allyl, and $R_{10}$ is hydrogen or fluoro;

(c) —CH_2—[furan]—CH_2—[phenyl];

(d) 4-phenoxy-2-butyn-2yl;
(e) 4-(benzyloxy)benzyl;
(f) 4-(4-fluorobenzyloxy)benzyl;

(g) —CH_2—[phenyl with CH_3 and phenyl substituents]; or (h) 4-(4-trifluoromethyl-2-pyridyloxy)benzyl; provided that:

$R_1$ is not 2,3-dichlorophenyl, 2,6-difluorophenyl, 2,6-di($C_1-C_4$ alkyl)phenyl, 2,4,6-tribromophenyl or 2,4,6-tri($C_1-C_4$ alkoxy)phenyl.

2. A compound according to claim 1 further in which $R_1$ is not 2,6-disubstituted phenyl, 2,3,6-trisubstituted phenyl or 2,4,6-trisubstituted phenyl.

3. A compound according to claim 1 in which $R_1$ is

[phenyl with $R_{11}$, $R_{12}$, $R_{13}$, $R_{14}$];

wherein $R_{11}$ is hydrogen, halogen, $C_1$-$C_4$ pl alkyl, $C_1$-$C_4$ haloalkyl, $C_1$-$C_4$ alkoxy, $C_1$-$C_4$ alkylthio, $C_1$-$C_4$ haloalkoxy, $C_1$-$C_4$ haloalkylthio, $C_2$-$C_5$ carboalkoxy, $C_2$-$C_5$ alkylcarbonyl, nitro or cyano; $R_{12}$ is hydrogen, halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, $C_3$-haloalkenoxy, nitro, cyano, $C_2$-$C_5$ alkylcarbonyl, $C_1$-$C_4$ alkylsulfonyl or $C_2$-$C_5$ carboalkoxy; and $R_{13}$ is hydrogen, halogen, $C_1$-$C_4$ haloalkyl or $C_1$-$C_4$ alkoxy, or $R_{11}$ and $R_{12}$ taken together are $C_2$-$C_4$ alkylene, $C_1$-$C_4$ alkyleneoxy, $C_1$-$C_4$ alkylenedioxy or halo-$C_1$-$C_3$ alkylenedioxy; and $R_{14}$ is hydrogen or fluoro; provided that $R_{11}$, $R_{12}$ and $R_{13}$ are not all hydrogen.

4. A compound according to claim 3 in which $R_{13}$ is hydrogen and $R_{11}$ and $R_{12}$ are other than hydrogen.

5. A compound according to claim 3 in which $R_{11}$ and $R_{13}$ are hydrogen.

6. A compound according to claim 3 in which $R_{12}$ and $R_{13}$ are hydrogen.

7. A compound according to claim 3 in which $R_{12}$ is a $C_1$-$C_2$ polyhaloalkoxy group containing at least one fluorine atom and $R_{13}$ is hydrogen or halogen.

8. A compound according to claim 7 in which $R_{11}$ is halogen, $C_1$-$C_4$ alkyl, $C_1$-$C_1$ haloalkyl, $C_1$-$C_4$ alkoxy or $C_1$-$C_4$ haloalkoxy; $R_{13}$ is hydrogen; and $R_{14}$ is halogen.

9. A compound according to claim 3 in which $R_{12}$ is trifluoromethoxy and $R_{11}$, $R_{13}$ and $R_{14}$ are all hydrogen.

10. A compound according to claim 3 in which $R_{11}$ is chloro, $R_{12}$ is fluoro, $R_{13}$ is hydrogen and $R_{14}$ is hydrogen.

11. A compound according to claim 1 in which $R_2$ is cyclopropyl, monomethyl-substituted cyclopropyl or tetramethyl-substituted cyclopropyl.

12. A compound according to claim 1 in which $R_3$ is

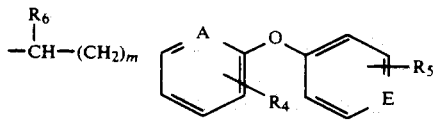

wherein m is 0 or 1, A and B are independently nitrogen or carbon, provided that A and E are not both nitrogen; $R_4$ is hydrogen or halo; $R_5$ is hydrogen, mono- or polyhalo, $C_1$-$C_4$ alkyl, $C_1$-$C_4$ alkoxy, trifluoromethyl, cyano, or $C_1$-$C_4$ alkylthio; and $R_6$ is hydrogen or methyl.

13. A compound according to claim 3 in which $R_3$ has the formula

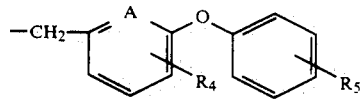

in which A is nitrogen or carbon and $R_4$ and $R_5$ are each independently hydrogen or halogen.

14. A compound according to claim 13 in which A is carbon, and $R_4$ and $R_5$ are both hydrogen.

15. A compound according to claim 13 in which A is carbon, $R_4$ is hydrogen and $R_5$ is halogen.

16. A compound according to claim 15 in which $R_5$ is fluoro.

17. A compound according to claim 13 in which A is carbon, $R_4$ is halogen and $R_5$ is hydrogen.

18. A compound according to claim 17 in which $R_4$ is fluoro.

19. A compound according to claim 13 in which A is carbon and $R_4$ and $R_5$ are both halogen.

20. A compound according to claim 19 in which $R_4$ is fluoro and $R_5$ is chloro.

21. A compound according to claim 19 in which $R_4$ and $R_5$ are both fluoro.

22. A method for controlling insects comprising applying to an insect, the locus of an insect or a locus at which insecticidal control is desired, an insecticidally effective amount of a compound according to claim 1.

23. A method for controlling insects according to claim 22 in which the insect is a member of the order Lepidoptera.

24. A method for controlling insects comprising applying to an insect, the locus of an insect, or a locus at which insecticidal control is desired, an insecticidally effective amount of a compound according to claim 3.

25. A method for controlling insects comprising applying to an insect, the locus of an insect or a locus at which insecticidal control is desired, an insecticidally effective amount of a compound according to claim 13.

26. An insecticidal composition comprising (a) an insecticidally effective amount of a compound according to claim 1; and (b) an insecticidally suitable diluent or carrier.

* * * * *

UNITED STATES PATENT AND TRADEMARK OFFICE
CERTIFICATE OF CORRECTION

PATENT NO. : 4,994,488

DATED : February 19, 1991

INVENTOR(S) : Michael D. Broadhurst, Karl J. Fisher, William G. Haag and Michael R. Leadbetter It is certified that error appears in the above-identified patent and that said Letters Patent is hereby corrected as shown below:

In Column 23, line 40, should be a single bond from $(CH_2)_m$ to the phenyl ring.

In Column 23, line 1, "$C_1$-$C_4$ pl alkyl, $C_1$" should read --- $C_1$-$C_4$ alkyl, $C_1$ ---.

In Column 23, line 25, "$C_1$-$C_1$ haloalkyl" should read --- $C_1$-$C_4$ haloalkyl ---.

In Column 23, line 45, "A and B" should read --- A and E ---.

Signed and Sealed this

Fifteenth Day of March, 1994

Attest:

BRUCE LEHMAN

*Attesting Officer*    *Commissioner of Patents and Trademarks*